(12) United States Patent
Wang et al.

(10) Patent No.: US 8,673,365 B2
(45) Date of Patent: Mar. 18, 2014

(54) HARD SURFACE CLEANING AND DISINFECTING COMPOSITION

(75) Inventors: Xue Wang, King of Prussia, PA (US); Keith R. Genco, Pottstown, PA (US)

(73) Assignee: Arkema Inc., King of Prussia, PA (US)

( * ) Notice: Subject to any disclaimer, the term of this patent is extended or adjusted under 35 U.S.C. 154(b) by 222 days.

(21) Appl. No.: 12/524,416

(22) PCT Filed: Jan. 4, 2008

(86) PCT No.: PCT/US2008/050166
§ 371 (c)(1),
(2), (4) Date: Oct. 26, 2009

(87) PCT Pub. No.: WO2008/094718
PCT Pub. Date: Aug. 7, 2008

(65) Prior Publication Data
US 2010/0055198 A1    Mar. 4, 2010

Related U.S. Application Data

(60) Provisional application No. 60/887,167, filed on Jan. 30, 2007.

(51) Int. Cl.
| | | |
|---|---|---|
| A01N 39/00 | (2006.01) |
| A61L 2/04 | (2006.01) |
| A61L 9/00 | (2006.01) |
| A61L 2/18 | (2006.01) |
| A61L 11/00 | (2006.01) |
| C11D 7/18 | (2006.01) |
| C11D 7/54 | (2006.01) |
| C11D 9/42 | (2006.01) |
| C11D 9/50 | (2006.01) |
| C11D 17/08 | (2006.01) |
| C11D 3/48 | (2006.01) |

(52) U.S. Cl.
USPC ........... 424/613; 424/616; 252/108; 252/109; 252/161; 422/1; 422/28; 510/370; 510/375; 510/382; 510/405; 510/419; 510/437

(58) Field of Classification Search
USPC ................. 424/616, 613; 252/108, 109, 161; 422/1, 28; 510/370, 375, 382, 405, 510/419, 437
See application file for complete search history.

(56) References Cited

U.S. PATENT DOCUMENTS

| | | | |
|---|---|---|---|
| 4,900,721 A | 2/1990 | Bansemir et al. | |
| 5,061,395 A * | 10/1991 | Meng ............................ | 510/423 |
| 5,891,392 A * | 4/1999 | Monticello et al. ............. | 422/28 |
| 6,106,774 A * | 8/2000 | Monticello et al. ............. | 422/28 |
| 6,686,324 B2 * | 2/2004 | Ramirez et al. ................ | 510/218 |
| 6,908,628 B2 | 6/2005 | Cabrera | |
| 7,199,090 B2 | 4/2007 | Koivisto et al. | |
| 8,143,309 B2 * | 3/2012 | Awad ............................ | 514/560 |
| 2002/0123445 A1 | 9/2002 | Dykstra et al. | |
| 2005/0109981 A1 | 5/2005 | Tucker et al. | |
| 2006/0193816 A1 | 8/2006 | Elfersy et al. | |
| 2006/0217286 A1 * | 9/2006 | Geoffroy et al. ............. | 510/490 |

FOREIGN PATENT DOCUMENTS

| | | |
|---|---|---|
| WO | WO 2005/089100 A2 | 9/2005 |
| WO | WO 2006/086271 A2 | 8/2006 |

* cited by examiner

*Primary Examiner* — Jane C Oswecki
(74) *Attorney, Agent, or Firm* — Steven D. Boyd

(57) ABSTRACT

A neutral pH aqueous ready-to-use cleaning and disinfectant compositions include hydrogen peroxide as an active disinfecting constituent including a C1-C6 monohydric alcohol, and a surfactant or surfactant mixture. Methods of cleaning and disinfecting surfaces are also disclosed.

13 Claims, No Drawings

HARD SURFACE CLEANING AND DISINFECTING COMPOSITION

FIELD OF THE INVENTION

The present invention relates to aqueous, ready to use cleaning and disinfectant compositions which include hydrogen peroxide and an alcohol as active disinfecting constituents, as well as methods for their production and methods for cleaning and disinfecting surfaces which include such compositions.

BACKGROUND OF THE INVENTION

Various ready to use cleaning and disinfecting compositions are known which include as germicidal active constituents one or more component such as alcohols, peroxides, phenolic containing materials, quaternary ammonium compounds as well as acids. However, many such known prior art compositions also frequently induce ocular and/or dermal irritation and this hampers their acceptance and use.

The current state of the art indicates the need for improved disinfecting compositions, particularly in a ready to use form, which may be classed as broad spectrum disinfecting compositions which also provide surface cleaning properties. The current state of the art also indicates the need for improved methods for disinfection, and preferably the combined disinfection and cleaning of hard surfaces. It is to these needs, as well as others, that the present invention is directed.

Hydrogen peroxide was first introduced into medical practice in 1856. Solutions of 3% wt. acidic hydrogen peroxide are used commercially as antiseptic treatment. For example U.S. Pat. No. 6,908,628 discloses a disinfecting and antiseptic composition that is a combination of hydrogen peroxide and lactic acid with surface active agents.

Short chain alcohols such as ethanol and isopropanol are known antiseptic agents. They usually work at high concentrations. For example WO 2005/030917 discloses a sanitizing foaming formulation with alcohol which employees over 40% v/v alcohol.

U.S. Pat. No. 5,891,392 discloses a ready to use hard surface cleaning and disinfecting composition which has an acidic pH containing hydrogen peroxide, a C1-C6 monohydric alcohol, a glycol ether or butoxypropanol, a nonionic surfactant and citric acid.

SUMMARY OF THE INVENTION

Hydrogen peroxide is known to be antiseptic under acidic pH. It has disinfectant properties against both gram-positive type bacteria such as *Staphylococcus aureus*, and gram-negative type bacteria such as *Salmonella choleraesuis* and *Pseudomonas aeruginosa*. However, the present inventors discovered that hydrogen peroxide alone could not effectively destroy gram positive bacteria such as *Staphylococcus aureus*. The present invention is directed to a neutral (pH 6-8) combination of hydrogen peroxide, alcohol and surfactants which was found to provide both broad antiseptic properties and cleaning properties. The combination of the present invention was found to provide effective antiseptic treatment for a wider variety of bacteria than hydrogen peroxide alone at neutral pHs. The combination of the present invention was also found to provide surface cleaning efficacies on many soils better than currently available commercial cleaning products.

The combination of the present invention comprises hydrogen peroxide, a $C_1$-$C_6$ monohydric alcohol and at least one surfactant wherein the combination has a neutral pH. By neutral pH is meant a pH of from about 6-8. The surfactant component of the present invention can be non-ionic, anionic, cationic and/or amphoteric or a combination thereof. The combination may optionally include one or more optional constituents such as solvents, hydrotropes, chelating agents, sequestrants, fragrances, coloring agents, thickening agents, gelling agents, pH buffers, pH adjusting agents, etc., known to those in the art as useful adjuvants in aqueous cleaning and disinfecting compositions.

A further aspect of the present invention is to provide an improved process for cleaning and disinfecting a hard surface in need of such treatment which includes the step of providing an effective amount of the aqueous cleaning and disinfecting compositions described herein to a hard surface requiring cleaning and/or disinfecting treatment. According to a preferred embodiment, the improved process utilizes the ready to use aqueous cleaning and disinfecting composition outlined above.

DETAILED DESCRIPTION OF THE INVENTION

The compositions of the invention are of neutral pH, ready to use aqueous cleaning and disinfecting compositions which provide both a good cleaning benefit as well as excellent disinfecting characteristics particularly to hard surfaces. In particularly preferred embodiments the disinfectant characteristics of the compositions are sufficient such that they may be classified as "hospital strength" disinfectant compositions, as they demonstrate excellent antimicrobial activity against both gram positive type bacteria such as *Staphylococcus aureus*, and gram negative type bacteria such as *Salmonella choleraesuis*. Thus the characteristics of both good cleaning and good disinfecting are provided in an aqueous cleaning composition having a neutral pH. Compositions having such constituents, which provide the effects described herein are not believed to have been hitherto known to the art.

The compositions according to the instant invention include 0.1-10% wt. of a $C_1$-$C_6$ monohydric alcohol. Mixtures of two or more such $C_1$-$C_6$ monohydric alcohols may also be used. Exemplary and preferred monohydric alcohols include methanol, ethanol, propanol, isopropanol and n-propanol of which isopropanol is most preferred. Such materials are widely commercially available. Desirably, $C_1$-$C_6$ monohydric alcohol constituent is present from about 1 to about 6% wt., and yet more desirably from about 2 to about 5% wt.; most desirably about 3% wt. of the $C_1$-$C_6$ monohydric alcohol constituent is present. These low amounts of monohydric alcohol(s) as described herein are preferred so to provide an overall reduction in the amount of volatile organic materials in the inventive compositions. Yet surprisingly, the inventive compositions provide excellent disinfecting properties.

The compositions of the present invention also include hydrogen peroxide as a primary disinfecting constituent. The hydrogen peroxide is present in concentrations from about 0.1 to 10% wt based on the total weight of the aqueous cleaning and disinfecting composition yet more desirably from about 2 to 5% wt.; most desirably about 3% wt. The amount of hydrogen peroxide may be increased slightly in order to allow for a slight loss of hydrogen peroxide during the shelf life of the cleaning and disinfecting composition.

The compositions according to the invention include 0.1-10% wt. of a surfactant. Useful surfactants which may be included in the concentrate compositions include nonionic, anionic, cationic and amphoteric surfactant compounds.

Non-ionic surfactants can include practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethoxy hydrophobic and hydrophilic elements may vary. Exemplary non-ionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

Particularly useful and preferred nonionic surfactants include alcohol alkoxylates, and alcohol ethoxylates based linear primary alcohols and linear secondary alcohols. These are preferred as they exhibit excellent compatibility with the other constituents which make up the invention, provide a good soil and stain releasing benefit, are relatively non-toxic to humans, and are not particularly irritating to the skin, eyes or mucosal tissues.

Examples of nonionic surfactants include but not limited to, ethoxylated and propoxylated alcohols, especially C10-20 alcohols, with 2 to 100 moles of ethylene oxide and/or propylene oxide per mole of alcohol, especially ethoxylates of primary alcohols containing about 8 to 18 carbon atoms in a straight or branched chain configuration with about 5 to 30 moles of ethylene oxide, for example, the ethoxylates of decyl alcohol, cetyl alcohol, lauryl alcohol, or myristyl alcohol; ethoxylates of secondary aliphatic alcohols containing 8 to 18 carbon atoms in a straight or branched chain configuration with 5 to 30 moles of ethylene oxide; condensates of aliphatic alcohols containing about 8 to abut 20 carbon atoms with ethylene oxide and propylene oxide; polyethylene glycol and polyethylene oxide; ethoxylated castor oil; ethoxylated hydrogenated castor oil; ethoxylated coconut oil; ethoxylated lanolin; ethoxylated tall oil; ethoxylated tallow alcohol; and ethoxylates of sorbitan esters. A particular example is the Neodol series (available form Shell Chemical Co.), typically linear alcohol ethoxylates with an average of 3-9 moles of ethoxylation. These surfactants provide excellent cleaning capability, hydrogen peroxide compatibility, formulation compatibility, in addition to their benign environmental profiles.

Other exemplary nonionic surfactants include but are not limited to substituted amine oxides and terpene type surfactants. Examples of amine oxides include alkyl amine oxides, alkoxylated amine oxide (e.g. Barlox 12i® available form Lonza, a lauryl amine oxide), and may include sulfonated or other types of substituents or amide/ester linkage. These surfactants provide excellent foaming property with improved cleaning efficacy. Examples of terpene type surfactants include limonene, substituted limonene and other terpene chemicals. These surfactants provide excellent solubility and cleaning efficacy against oily stains.

Exemplary anionic surfactants include but are not limited to alkalimetal salts or the magnesium salts of: alkyl sulfates, alkyl ether sulfates, alkylamido ether sulfates, alkylaryl polyether sulfates, monoglyceride sulfates, alkylsulfonates, alkylamide sulfonates, alkylarylsulfonates, olefinsulfonates, paraffin sulfonates, alkyl sulfosuccinates, alkyl ether sulfosuccinates, alkylamide sulfosuccinates, alkyl sulfosuccinamate, alkylsulfoacdetates, alkyl phosphates, alkyl ether phosphates, acyl sarcosinates, acyl isethionates, and N-acyl taurates. Ammonium salts, amine salts, and aminoalcohol salts of the above compounds should be excluded from the list due to their incompatibility with hydrogen peroxide.

Examples of the anionic surfactants include but are not limited to sulfates and sulfates of ethoxylates, sodium cetyl sulfate, sodium lauryl sulfate, sodium myristyl sulfate, sodium stearyl sulfate, sodium dodecylbenzene sulfonate, and sodium polyoxyethylene lauryl ether sulfate.

Amphoteric surfactants include but are not limited to one or more surfactant compositions with zwitterionic head groups, including betaines, ethylene oxide condensates, triglycines, and fatty acid amides. An example of amphoteric surfactants is lauryl dimethylammonium acetic acid.

Cationic surfactants include, but are not limited to, surfactants which contain ammonium sulfonium, phosphonium, pyridinium, quinolinium, and viologen groups. Examples include substituted ammonium salt with linear or branched hydrophobic, aliphatic, aryl aliphatic or aliphatic aryl substituents, and may include one or more amide or ester linkages.

The surfactant constituent according to the invention may be a single surfactant or a plurality of surfactants which comprise 0.1 to 10% wt based on the total weight of the aqueous cleaning and disinfecting composition yet more desirably from about 1 to 4% wt.; most desirably about 1-2% wt.

The cleaning and disinfecting compositions of the present invention are adjusted to a neutral pH, generally from 6-8, but desirably are maintained at a pH of about 7. Such may be achieved primarily by the addition of effective amounts of a neutralizing agent compatible with hydrogen peroxide and the formulation noted here. Examples include but are not limited to alkali metal hydroxide, alkali metal phosphates, polyphosphates, pyrophosphates, triphosphates, tetraphosphates, silicates, metasilicates, polysilicates, and mixtures thereof. Such pH may also be maintained, for example, by the inclusion of one or more pH buffers as described with reference to the optional constituents.

As the inventive compositions are aqueous in nature, water is a major constituent. Desirably deionized water is used.

The compositions of the invention may include minor amounts of one or more optional constituents, as described hereinafter.

Additives such as solvents and hydrotropes may be included. These additives can help stabilizing the surfactants and allow them to remain soluble in an aqueous formulation. In addition, they can help improving cleaning or disinfectant efficacy of the formulations. These compounds include but are not limited to alkyl alcohols, alkyl ethers, glycol ethers, short chain alkyl or aromatic sulfates, short chain alkyl or aromatic sulfonates and mixtures thereof. An example of a hydrotrope is sodium xylene sulfonate and an example of a solvent is alkyl diglycol ether with ethyl, butyl and other alkyl substituents.

Hydrogen peroxide stabilizers such as chelants and sequestrants may also be included. Hydrogen peroxide is not stable in the presence of trace amount of transition metal ions and some organic and inorganic compounds. Impurities from surfactants, other additives and water can all decompose hydrogen peroxide. Additional chelants and sequestrants may be added to help isolate hydrogen peroxide from these impurities, and thus improve the stability of hydrogen peroxide. These compounds can also soften the water and help improving the general cleaning efficacy of surfactants. Chelating agents and sequestrants include but are not limited to acids or alkali metal salts of carboxylic acids with 1 to 9 carboxylic substituents, polyacrylates, phosphonic acids, pyrophosphates, polyphosphates, silicates, polysilicates, substituted silicates, stannates, polystannates, substituted stannates. Examples of chelating agents include but are not limited to acids, alkali metal salts of the following compounds: citric acid, salicylic acid, EDTA, DTPA, stannate, iminodisuccinic acid etc. and the mixture there of.

Foaming agents, and foam stabilizing agents may be provided. As is known to the art, such may be commercially desirable in compositions according to the invention. Such may be especially desirable where the composition is packaged in a pressurized device, i.e., an aerosol canister or in a hand-held pumpable container (such as a hand-held trigger spraying vessel), so that upon the application of the composition to the stain a foaming action is observed by the consumer when dispensed onto a surface. Known foaming agents may be used including the following exemplary compositions: alkyl sulfates, alkyl sulfonates, amine oxides, alkanolamides, as well as others known to the art.

Further optional, but desirable constituents include fragrances, natural or synthetically produced. Such fragrances may be added in any conventional manner, admixing to a composition or blending with other constituents to form a composition, in amounts which are useful to enhance or impart the desired scent characteristics to the composition.

In compositions which include a fragrance, it is frequently desirable to include a fragrance solubilizer which assists in the dispersion, solution or mixing of the fragrance constituent in an aqueous base. These include known art compounds, such as condensates of 2 to 30 moles of ethylene oxide with sorbitan mono- and tri-$C_{10}$-$C_{20}$ alkanoic acid esters which are also known as nonionic surfactants. Further examples of such suitable surfactants include water soluble nonionic surfactants of which many are commercially known and by way of non-limiting example include the primary aliphatic alcohol ethoxylates, secondary aliphatic alcohol ethoxylates, alkylphenol ethoxylates and ethylene-oxide-propylene oxide condensates on primary alkanols, and condensates of ethylene oxide with sorbitan fatty acid esters. This fragrance solubilizer component is added in minor amounts, so as to be effective in aiding in the solubilization of the fragrance component, but not in any significantly greater proportion, such that it would be considered as a detergent constituent. Such minor amounts recited herein are generally up to about 0.3% by weight of the total composition but is more generally an amount of about 0.1% by weight and less, and preferably is present in amounts of about 0.05% by weight and less.

Further optional, but advantageously included constituents are one or more coloring agents which find use in modifying the appearance of the compositions and enhance their appearance from the perspective of a consumer or other end user. Known coloring agents may be incorporated in the compositions in any effective amount to improve or impart to compositions a desired appearance or color. Such coloring agents may be added in a conventional fashion, i.e., admixing to a composition or blending with other constituents used to form a composition.

The use of one or more known pH adjusting agents, including agents known to the art such as mineral acids, basic compositions, and organic acids may be used in minor amounts. An exemplary composition includes citric acid, such as is available in an anhydrous salt form of an alkali metal citric acid. The addition of an effective amount of a pH adjusting agent is useful in establishing a targeted pH range for compositions according to the invention.

An effective amount of a pH buffering composition so to maintain the pH of the inventive compositions may also be added. While the composition of the invention generally does not require a pH buffering composition, its use may provide the benefit of hard water ion sequestration, should the inventive composition be diluted with further water by the consumer or other end user. Any pH buffering compound or pH buffer composition which is compatible with the aqueous compositions taught herein may be used, and many of these are well known to the art. Examples of such useful pH buffer compounds and/or pH buffering systems or compositions include the alkali metal phosphates, polyphosphates, pyrophosphates, triphosphates, tetraphosphates, silicates, metasilicates, polysilicates, carbonates, hydroxides, and mixtures thereof. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, and their alkali metal salts. Such buffers keep the pH ranges of the compositions of the present invention within acceptable limits. Others, not particularly elucidated here may also be used. Preferably, citric acid, such as is available in an anhydrous salt form of an alkali metal citric acid is added as it is readily commercially available, and effective. The addition of a buffering agent is desirable in certain cases wherein long term, i.e., prolonged storage, is to be anticipated for a composition, as well as ensuring the safe handling of said aqueous composition.

Further useful constituents which may be included are one or more thickening and/or gelling agents which may be added to the hard surface cleaning compositions according to the present invention in order to modify the viscous and/or thixotropic properties thereof. For example, in certain applications it is contemplated that it may be desirable to provide compositions which are more viscous than water, whether for aesthetic or functional reasons. For example, the addition of a suitable amount of a gelling agent may be desired not only for aesthetic reasons but also to limit the spreading of the composition as it is applied to a surface. This function is desirable in providing a means to apply the composition over a limited area, such as directly onto a stain, without applying an excess onto the surrounding area of a surface. This function also aids in the surface retention time on non-horizontal surface, ensuring that the cleaning composition is in contact with a stained surface without flowing off too rapidly. Similarly, thixotropic properties may also be desired under certain circumstances. In order to provide such functional features to the composition, known thickening and gelling agents including, but not limited to, cellulose compounds, xanthan gums, polymers and/or clays may be added.

As denoted above, the aqueous cleaning and disinfecting compositions according to the invention may include minor amounts of one or more optional additives including those known to the art as useful in such compositions. These optional constituents, if present, desirably comprise not more than a total of about 4% wt. based on the total weight of the inventive compositions and more desirably are present in lesser amounts.

Aqueous cleaning and disinfecting compositions according to the invention are desirably provided as a ready to use product which may be directly applied to a hard surface. By way of example, hard surfaces suitable include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry. Hard surfaces which are to be particularly denoted are lavatory fixtures such as shower stalls, bathtubs and bathing appliances (racks, curtains, shower doors, shower bars) toilets, bidets, wall and flooring surfaces especially those which include refractory materials and the like. Further hard surfaces which are to be denoted are those associated with kitchen environments and other environments associated with food preparation, including cabinets and countertop surfaces as well as walls and floor surfaces especially those which include refractory materials, as well as plastics, Formica®, Corian® and stone. Hard surfaces which are to be most particularly denoted include hard surfaces associated with hospital environments, medical laboratories and medical treatment environments. These include hard surfaces found for example in operating theatres, surgical areas and surgical preparation areas as well as surgical recovery areas, surfaces found on moveable equipment, i.e., gurneys, moveable equipment such as instruments, and moveable stands, moveable beds, wheelchairs, and the like, as well as surfaces found of equipment which is not normally moved including operating and examining tables, instruments such as non-moveable monitoring equipment, anesthesia dispensing equipment, beds and the like. Such hard surfaces described above are to be understood as being recited by way of illustration and not be way of limitation.

The compositions according to the invention are useful in the cleaning and/or disinfecting of surfaces, especially hard surfaces, having deposited soil thereon. In such a process, cleaning and disinfection of such surfaces comprises the step of applying a stain releasing and disinfecting effective amount of a composition as taught herein to the stained surface. Afterwards, the compositions are optionally but desirably wiped, scrubbed or otherwise physically contacted with the hard surface, and further optionally, may be subsequently rinsed from such a cleaned and disinfected hard surface.

The hard surface cleaning and disinfecting composition provided according to the invention is conveniently provided as a ready-to-use product in a manually operated spray dispensing container. Such a typical container is generally made of synthetic polymer plastic material such as polyethylene, polypropylene, polyvinyl chloride or the like and includes spray nozzle, a dip tube and associated pump dispensing parts and is thus ideally suited for use in a consumer "spray and wipe" application. In such an application, the consumer generally applies an effective amount of the cleaning composition using the pump and, within a short time thereafter, wipes off the treated area with a rag, towel, or sponge, usually a disposable paper towel or sponge. In certain applications, however, especially where undesirable stain deposits are heavy, the cleaning composition according to the invention may be left on the stained area until it has effectively loosened the stain deposit after which it may then be wiped off, rinsed off, or otherwise removed. For particularly heavy deposits of such undesired stains, multiple applications may also be used.

In a yet further embodiment, the compositions according to the invention may also be formulated so that they are provided as an "aerosol" type product which is discharged from a pressurized aerosol container. If the inventive compositions are used in an aerosol type product, it is preferred that corrosion resistant aerosol containers such as coated or lined aerosol containers be used. Known art propellants such as liquid propellants as well as propellants of the non-liquid form, i.e., pressurized gases, including carbon dioxide, air, nitrogen, hydrocarbons as well as others may be used. Also, while satisfactory for use, fluorocarbons may be used as a propellant but for environmental and regulatory reasons their use is preferably avoided. In this embodiment, the composition is dispensed by activating the release nozzle of said aerosol type container onto the stain and/or stain area and, in accordance with a manner as above-described a stain is treated and removed.

Whereas compositions of the present invention are intended as a ready to use product and is not specifically intended to be diluted into a further volume of water, nothing in this specification shall be understood as to limit the use of said compositions with a further amount of water to form a cleaning and disinfecting solution. In such a proposed diluted cleaning solution, the greater the proportion of water added to form said cleaning and disinfecting dilution, the greater may be the reduction of the rate and/or efficacy of the thus formed cleaning and disinfecting solution in the treatment of a hard surface. Thus, an undesirable reduction in disinfectant efficacy may result and accordingly, longer residence times on the surface to be treated may be required in order to satisfactorily loosen stains and soils and provide a sufficient disinfecting effect. Alternatively, the usage of greater amounts and/or multiple treatments with such a disinfecting solution may be necessitated. Conversely, nothing in the specification shall be also understood to limit the forming of a concentrated cleaning and disinfecting composition based upon the composition described above. Such a concentrated composition is essentially the same as the compositions described above except in that they include a lesser amount of water.

EXAMPLES

The testing was performed in accordance with the protocols outlined in "Use-dilution Method", Protocols 955.14, 955.15 and 964.02 described in Chapter 6 of "Official Methods of Analysis", 16.sup.th Edition, of the Association of Official Analytical Chemists; "Germicidal and Detergent Sanitizing Action of Disinfectants", 960.09 described in Chapter 6 of "Official Methods of Analysis", 15.sup.th Edition, of the Association of Official Analytical Chemists; or American Society for Testing and Materials (ASTM) E 1054-91 the contents of which are herein incorporated by reference. This test is also commonly referred to as the "AOAC Use-Dilution Test Method". Testing was conducted starting with $10^5$ to $10^6$ CFU/ml bacteria concentration, 10 ml of the cleaning composition described in each example and test protocol outlined in the "AOAC Use-dilution Method".

Example 1

Testing was undertaken of hydrogen peroxide alone at acid (4.4) and neutral (7.7) pH. It was found that, hydrogen peroxide alone was not effective at killing gram positive bacteria *Staphylococcus aureus* under the acidic pH or at the neutral pH. (Table 1).

TABLE 1

The disinfection with 3% hydrogen peroxide at pH 4 and 8

| Solution (% w/w) | pH | Time (min) | S. aureus (CFU/ml) | P. aeruginosa (CFU/ml) | S. choleraesuis (CFU/ml) |
|---|---|---|---|---|---|
| 3% $H_2O_2$ | 4.4 | 0 | $1.6 \times 10^5$ | $1.7 \times 10^5$ | $2.9 \times 10^5$ |
|  |  | 5 | $4.3 \times 10^3$ [*1] | N.D [*2] | ND |
| 3% $H_2O_2$ | 7.7 | 0 | $1.3 \times 10^5$ | $1.5 \times 10^5$ | $2.4 \times 10^5$ |
|  |  | 5 | $6.0 \times 10^2$ | N.D. | N.D. |

[*1] The data is the average from two replicates
[*2] N.D. = "not detected" means it is below the detection limit Example 2

Testing was undertaken of hydrogen peroxide with a surfactant. The combination was found to effectively kill gram positive bacteria under the acidic pH. (Table 2). However, it is not equally effective under the neutral pH. (Table 3)

TABLE 2

The disinfection of $H_2O_2$ + Surfactant at pH 4

| Solution (% w/w) | pH | Time (min) | S. aureus (CFU/ml) | P. aeruginosa (CFU/ml) | S. choleraesuis (CFU/ml) |
|---|---|---|---|---|---|
| Surfactant*[3] alone | 4 | 0 | $1.5 \times 10^6$ | $1.3 \times 10^6$ | $1.2 \times 10^6$ |
| | | 5 | $5.0 \times 10^2$ | N.D | N.D. |
| Surfactant + 3% $H_2O_2$ | 4 | 0 | $1.5 \times 10^6$ | $1.3 \times 10^6$ | $1.2 \times 10^6$ |
| | | 5 | N.D. | N.D. | N.D. |

*[3]Surfactant blend is: 0.5% amine oxide (Barlox ® 12i) + 0.5% long chain sulfonate (SLS) + 0.5% nonionic surfactant (Neodol ® 91-8)

TABLE 3

The disinfection of $H_2O_2$ + Surfactant at pH 7

| Solution (% w/w) | pH | Time (min) | S. aureus (CFU/ml) | P. aeruginosa (CFU/ml) | S. choleraesuis (CFU/ml) |
|---|---|---|---|---|---|
| Surfactant*[4] alone | 7 | 0 | $1.7 \times 10^5$ | $1.7 \times 10^5$ | $1.8 \times 10^5$ |
| | | 5 | $3.8 \times 10^4$ | N.D | N.D. |
| Surfactant + 3% $H_2O_2$ | 7 | 0 | $1.7 \times 10^5$ | $1.6 \times 10^5$ | $1.6 \times 10^5$ |
| | | 5 | $2.4 \times 10^4$ | N.D. | N.D. |

*[4]Surfactant blend is: 0.5% amine oxide (Barlox ® 12i) + 0.5% long chain sulfonate (SLS) + 0.5% nonionic surfactant (Neodol ® 91-8) + 0.2% citric acid Example 3

Isopropanol is a known antiseptic at high concentration. Testing of isopropanol was undertaken at low concentration (e.g. 3%). It was found to exhibit slight disinfectant property. Table 4 summarizes the results

TABLE 4

The disinfection data of Isopropanol + Surfactant at pH 7

| Solution (% w/w) | pH | Time (min) | S. aureus (CFU/ml) | P. aeruginosa (CFU/ml) | S. choleraesuis (CFU/ml) |
|---|---|---|---|---|---|
| Surfactant*[5] + 3% isopropanol | 7 | 0 | $1.4 \times 10^5$ | $1.4 \times 10^5$ | $1.3 \times 10^5$ |
| | | 5 | $8.6 \times 10^2$ | 15 | 90 |

*[5]Surfactant blend is 0.5% amine oxide (Barlox ® 12i) + 0.5% long chain sulfonate (SLS) + 0.5% nonionic surfactant (Neodol ® 91-8) + 0.2% citric acid + 0.5% Limonene Example 4

A combination, in accordance with the present invention of:

| Amine Oxide Amphoteric surfactant | 0.50% |
| EO non ionic surfactant | 0.50% |
| Long chain anionic surfactant | 0.50% |
| Limonene | 0.50% |
| Isopropanol | 3.0% |
| $H_2O_2$ Peroxal CLG | 3.0% | was evaluated for both disinfecting properties and surface cleaning effectiveness. This formulation exhibited broad-spectrum disinfection properties against both gram-positive and gram-negative bacteria at neutral pH. (Table 5A). It also exhibited sufficient cleaning property in comparison to commercial cleaning products (e.g. 409® by Clorox). (Table 5B)

TABLE 5A

The disinfection data of Isopropanol + Surfactant at pH 7

| Solution (% w/w) | pH | Time (min) | S. aureus (CFU/ml) | P. aeruginosa (CFU/ml) | S. choleraesuis (CFU/ml) |
|---|---|---|---|---|---|
| Surfactant*[6] + 3% isopropanol + 3% $H_2O_2$ | 7 | 0 | $1.2 \times 10^6$ | $1.0 \times 10^6$ | $1.2 \times 10^6$ |
| | | 5 | N.D.*[7] | N.D. | N.D. |

*[6]Surfactant blend is 0.5% amine oxide (Barlox ® 12i) + 0.5% nonionic surfactant (Neodol ® 91-8) + 0.2% citric acid + 0.5% Limonene
*[7]A second test was done with 10 minutes reaction time and duplicates, similar results were obtained.

TABLE 5B

The cleaning data of our formulation*[7]

| | Cleaning Efficacy (% stain removal) | |
|---|---|---|
| Stain | Composition in 5A | 409 (by Clorox) |
| Wine | | |
| On Painted Wallboard | 26.9 | 14.5 |
| On Vinyl Tile | 44.9 | 56.7 |
| Coffee | | |
| On Painted Wallboard | 30.2 | −8.0 |
| On Vinyl Tile | 82.4 | 80.8 |
| Cran-Grape Juice | | |
| On Painted Wallboard | 59.7 | 11.1 |
| Pencil | | |
| On Painted Wallboard | 61.6 | 56.5 |
| On Countertop | 72.8 | 78.5 |
| Oily soil | | |
| On Vinyl tile | 41.0 | 69.6 |
| On Countertop | 7.8 | 32.3 |

*[7]The cleaning data was obtained by an independent lab with cleaning method as set forth in ASTM D4488-A3.

Having described the invention, we now claim the following and their equivalents.

What is claimed is:

1. A ready-to-use aqueous cleaning and disinfecting composition which comprises:
    0.1-10% wt. of a $C_1$-$C_6$ monohydric alcohol;
    0.1-10% wt. of a surfactant mixture comprising an amine oxide, a long chain sulfonate and a nonionic surfactant;
    0.1-10% wt. of hydrogen peroxide;
    to 100% wt. water;
    wherein the said composition is at a pH of about 7 and said composition exhibits broad spectrum disinfecting properties against both gam-positive and gram-negative bacteria.

2. The ready-to-use aqueous cleaning and disinfecting composition according to claim 1 which further comprises: 0-4% wt. of one or more optional constituents selected from solvents, hydrotropes, chelating agents, sequestrants, foaming agents, foam stabilizing agents, fragrances, fragrance solubilizers, coloring agents, pH adjusting agents, pH buffering agents, thickening agents and gelling agents.

3. The ready-to-use aqueous cleaning and disinfecting composition according to claim 1 which comprises 2-5% wt. of hydrogen peroxide.

4. The ready-to-use aqueous cleaning and disinfecting composition according to claim 1 which comprises 1-6% wt. of a $C_1$-$C_6$ monohydric alcohol.

5. The ready-to-use aqueous cleaning and disinfecting composition according to claim 4 which comprises 2-5% wt. of a $C_1$-$C_6$ monohydric alcohol.

6. The ready-to-use aqueous cleaning and disinfecting composition according to claim 1 which is effective against gram-positive type pathogenic bacteria.

7. The ready-to-use aqueous cleaning and disinfecting composition according to claim 1 which is effective against gam-negative type pathogenic bacteria.

8. The ready-to-use aqueous cleaning and disinfecting composition according to claim 1 which is effective against at least one bacteria selected from: *Staphylococcus aureus, Salmonella choleraesuis*, or *Pseudomonas aeruginosa*.

9. The ready-to-use aqueous cleaning and disinfecting composition according to claim 8 which is effective against at least two bacteria selected from: *Staphylococcus aureus, Salmonella choleraesuis*, or *Pseudomonas aeruginosa*.

10. The ready-to-use aqueous cleaning and disinfecting composition according to claim 9 which is effective against at all three bacteria: *Staphylococcus aureus, Salmonella choleraesuis*, or *Pseudomonas aeruginosa*.

11. The process for the disinfection of hard surfaces wherein the presence of gram-negative type pathogenic bacteria is suspected which comprises the process step of: applying a germicdally effective amount of the composition according to claim 1.

12. The process for the disinfection of hard surfaces wherein the presence of gram-positive type pathogenic bacteria is suspected which comprises the process step of: applying a germicdally effective amount of the composition according to claim 1.

13. The process for the disinfection of hard surfaces wherein the presence of one or more bacteria selected from *Staphylococcus aureus, Salmonella choleraesuis*, or *Pseudomonas aeruginosa* is suspected which comprises the process step of:

applying a germicdally effective amount of the composition according to claim 1.

\* \* \* \* \*